US00PP08670P

United States Patent [19]

Austin

[11] Patent Number: Plant 8,670

[45] Date of Patent: Apr. 5, 1994

[54] ROSE PLANT 'AUSPRIMA'

[75] Inventor: David C. H. Austin, Wolverhampton, England

[73] Assignee: David Austin Roses Limited, Wolverhampton, England

[21] Appl. No.: 954,883

[22] Filed: Sep. 30, 1992

[51] Int. Cl.[5] ..... A01H 5/00

[52] U.S. Cl. ..... Plt./1

[58] Field of Search ..... Plt. 1, 29

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A shrub rose plant having compact, bushy growth, deep pink flowers, very regular flat flowers, and being very floriferous.

1 Drawing Sheet

The present invention relates to a new and distinct variety of shrub rose plant of the *Rosa hybrida* class which was originated by me by crossing the variety Mary Rose, with the variety The Squire.

The primary objective of this breeding was to produce a new rose variety having pink, quartered, scented flowers on a bushy plant which repeatedly flowers. The objective was substantially achieved along with other desirable improvements as evidenced by the following unique combination of characteristics which are outstanding in the new variety and which distinguish it from its parents, as well as from all other varieties of which I am aware:

1. Compact growth;
2. Deep pink flowers;
3. Very regularly flat flowers; and
4. Very floriferous.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Mary Rose.

*Pollen parent.*—The Squire.

Classification:

*Botanical.*—*Rosa hybrida.*

*Commercial.*—Shrub.

FLOWER

Observations made from specimens grown in a garden environment in Albrighton, Wolverhampton, England in August 1991.

Blooming habit: Recurrent.

Bud:

*Size.*—About 1" long when the petals start to unfurl.

*Form.*—The bud form is globular, pointed ovoid.

*Color.*—When sepals first divide, the bud color is violet brown 11F8 to brownish violet 11D8. When half blown, the upper and lower sides of the petals are ruby 12C7, but brighter on the outer edge changing to deep red 11C8 in the center.

*Sepals.*—Color: Greyish green 29E7 with violet brown blush 11E7. Surface texture: Leathery and ridged. There are three slightly appendaged sepals. There are two unappendaged sepals with hairy edges.

*Receptacle.*—Color: Deep green 29D8. Shape: Cup shaped. Size: Small to medium, about ⅜ inches × ⅜ inches. Surface: Smooth.

*Peduncle.*—Length: Medium to short, averaging about 1¼-2". Surface: Glandular. Color: Medium, greyish green 30D7 with brownish violet blush 11D7. Strength: Erect.

Bloom:

*Size.*—Medium. Average open size is 2½".

*Borne.*—Singly, several together. If in clusters: Irregular shape, averaging 1-6 flowers per cluster.

*Stems.*—Medium. Average length is 18 to 24 inches.

*Form.*—When first open: Globular with flat top. Permanence: Flattens, outer petals curl back.

*Petalage.*—Number of petals under normal conditions: 65 to 75.

*Color.*—The upper and lower sides of the petals are Greyish ruby 12C7/8 on the outer edge of the petal changing to greyish rose 12B4/5 towards the center of the petal. The color of the base of the petals is yellow 2A4. The major color on the upper side is Greyish ruby 12C7.

*Variegations.*—None.

*Discoloration.*—The general tonality at the end of the first day: Very little change. At the end of the third day, slightly greyer and deeper.

*Fragrance.*—Strong, tea rose.

Petals:

*Texture.*—Fleshy, thick.

*Shape.*—Round, deltoid to heart-shaped.

*Form.*—Cupped.

*Arrangement.*—Quartered, with few petaloids in the center.

*Persistence.*—Petals drop off cleanly before drying.

*Lastingness.*—On the plant: About 7 to 10 days. As a cut flower: About 5 to 7 days.

Reproductive parts:

*Anthers.*—Size: Medium. Quantity: Many (70). Color: Yellow. Arrangement: Tucked in calyx or partly so, mixed with petaloids.

*Filaments.*—Color: Yellow and cerise blush 12C8.

*Pollen.*—Color: Gold yellow.

*Styles.*—Color: Pale green 30A3.

*Stigmas.*—Color: Pale yellow 2A4.

Form: Shrub.

Growth: Medium, upright, compact, bushy.

Plant height: About 2'6".

Foliage:

*Number of leaflets on normal mid-stem leaves.*—5.

*Size.*—Medium, about 1½" long×1" wide.

*Quantity.*—Normal.

*Color.*—New foliage: Greyish green 28E7 with violet brown 11E8 on margins. Old foliage: Dark green 28F7.

Leaflets:

*Shape.*—Base is round, oval, cuspidate apex.

*Texture.*—Upper side: Leathery.

*Edge.*—Serrated.

*Serration.*—Single, small.

*Petiole rachis.*—Color: Greyish green 30E7 and brownish violet 11D8 blush.

*Petiole underside.*—With prickles, 0 to 2 per internode.

*Stipules.*—Medium, about ½ to ¾" long.

*Disease resistance.*—Resistant to mildew and blackspot under normal growing conditions at Albrighton, Wolverhampton, England.

Wood:

*New wood.*—Color: Deep green 29E8 and Violet brown blush 10E7. Bark: Smooth.

*Old wood.*—Color: Dark green 29F7. Bark: Smooth, slightly ridged.

Prickles:

*Quantity.*—On main canes from base: Many. On laterals from main canes: Ordinary.

*Form.*—Medium, hooked downward.

*Color when young.*—Violet brown 10E8.

*Position.*—Evenly distributed.

Small prickles:

*Quantity.*—On main stalks: Few. On laterals: Few.

*Color.*—Brown.

I claim:

1. A new and distinct variety of shrub rose plant of the *Rosa hybrida* class, substantially as herein shown and described, characterized particularly as to novelty by the unique combination of its compact bushy growth, deep pink flowers, very regular flat flowers, and its being very floriferous.

* * * * *

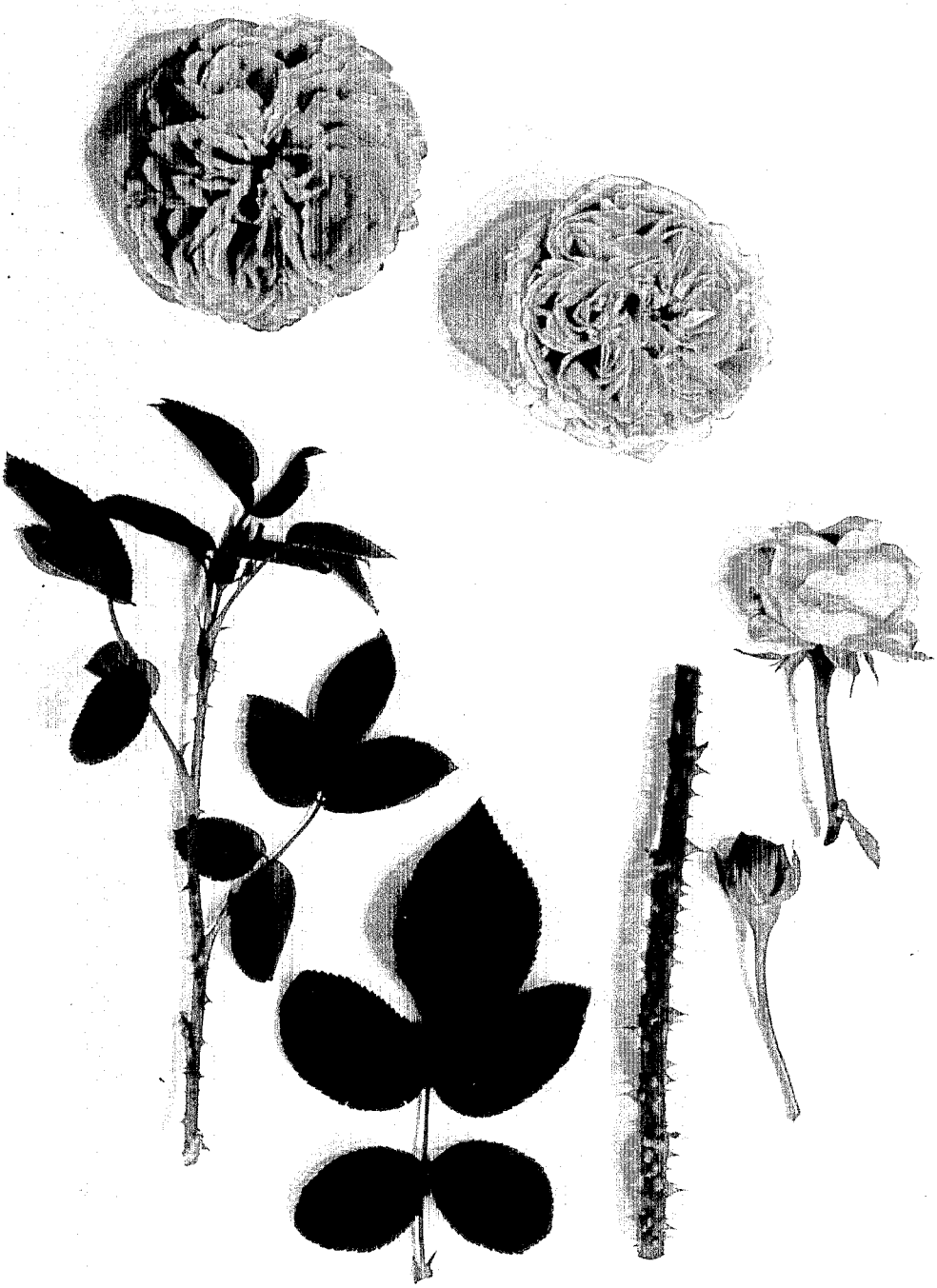
A. L. Sprima